United States Patent
Dougill et al.

(10) Patent No.: US 6,776,163 B2
(45) Date of Patent: Aug. 17, 2004

(54) NASAL CANNULAE

(75) Inventors: Silvia Beatriz Dougill, London (GB); Christian Juan Feldermann, Abberley (GB)

(73) Assignee: The BOC Group, plc, Windlesham (GB)

(*) Notice: Subject to any disclaimer, the term of this patent is extended or adjusted under 35 U.S.C. 154(b) by 0 days.

(21) Appl. No.: 10/378,762

(22) Filed: Mar. 4, 2003

(65) Prior Publication Data

US 2003/0168067 A1 Sep. 11, 2003

(30) Foreign Application Priority Data

Mar. 6, 2002 (GB) .............................................. 0205271
May 23, 2002 (GB) .............................................. 0211938

(51) Int. Cl.$^7$ ............................................. A61M 15/08
(52) U.S. Cl. .............................. 128/207.18; 128/207.13
(58) Field of Search ..................... 128/200.27, 200.28, 128/201.15, 201.23, 201.26, 203.29, 204.12, 206.11, 206.12, 206.18, 206.21, 206.28, 207.13, 207.18

(56) References Cited

U.S. PATENT DOCUMENTS

| 4,660,555 | A |   | 4/1987 | Payton |            |
|-----------|---|---|--------|--------|------------|
| 4,915,105 | A | * | 4/1990 | Lee .......................... | 128/205.27 |
| 6,119,694 | A | * | 9/2000 | Correa et al. ........... | 128/207.13 |
| 6,247,470 | B1 | * | 6/2001 | Ketchedjian ........... | 128/200.28 |
| 6,418,928 | B1 | * | 7/2002 | Bordewick et al. ..... | 128/205.25 |
| 6,431,172 | B1 | * | 8/2002 | Bordewick ............. | 128/207.18 |
| 6,478,026 | B1 | * | 11/2002 | Wood ..................... | 128/207.18 |
| 6,595,207 | B1 | * | 7/2003 | McDonald et al. ..... | 128/200.28 |
| 6,644,315 | B2 | * | 11/2003 | Ziaee ..................... | 128/206.21 |

FOREIGN PATENT DOCUMENTS

| WO | WO 82/01823 | 6/1982 |
| WO | WO 92/20392 | 11/1992 |
| WO | WO 97/21466 | 6/1997 |

* cited by examiner

*Primary Examiner*—Henry Bennett
*Assistant Examiner*—Teena Mitchell
(74) *Attorney, Agent, or Firm*—Philip VonNeida

(57) ABSTRACT

A nasal cannula for use in administering a gas under pressure through a nasal passage of a user comprises at least one tubular nasal prong assembly. The assembly includes an inner tubular prong 4 having a distal end to be placed in or adjacent the nasal passage and a proximal end for connection to a supply line 2 for the gas, and also includes an outer sleeve 8 extending over at least a portion of the inner tubular prong 4 to define therewith an annular passage 10 in communication with supply line 2. The arrangement is such that when gas flows through the supply line 2 most will flow out of the distal end of the prong 4 but some will pass through the annular passage 10 to form a shrouding stream.

2 Claims, 2 Drawing Sheets

NASAL CANNULAE

BACKGROUND OF THE INVENTION

Conventional nasal cannulae are used for the inhalation of oxygen or breathable gas mixtures containing oxygen. Some are aimed at semi-mobile users who can gain a degree of independence by using the cannulae together with mobile gas dispensers. Other users include those who work in hostile environments and require the delivery of a breathable gas whilst in the hostile environment.

Although the use of such nasal cannulae particularly for semi-mobile users are clearly advantageous, they can also present problems due to air entrainment with the subsequent dilution of the delivered gas.

This problem has been addressed by the use of masks which can regulate the amount of air entrained. The main drawbacks to the use of these known masks are:

uncomfortable to wear, leading possibly to necrosis heavy and bulky complicated to use unaesthetic.

It is known from WO-A-92/20392 for a nasal cannula to include a tubular insert element having a distal portion to be placed in a nasal passage and a proximal portion for connection to a supply line for oxygen or an oxygen-enriched gas. The distal portion is formed of a flexible and resilient material and has a divergent, generally frusto-conical configuration. The cannula provides a positive and comfortable fit in the nasal passage and is conveniently used with high humidity, high flowrate oxygen-enriched air supplied by oxygen-concentrators employing gas separation membranes.

Although the tubular insert element is conical in shape, air can be entrained through the gap between the nasal passage and the cone thereby decreasing the oxygen concentration of the inhaled gas.

BRIEF SUMMARY OF THE INVENTION

The present invention relates to nasal cannulae for the delivery of a gas or gas mixture under pressure to the nasal passages of a patient or user.

For the avoidance of doubt the use of the term "gas" throughout this specification is intended not only to embrace a single gas, for example, oxygen but also gas mixtures, for example, mixtures of oxygen/nitrogen or oxygen/helium.

It is an aim of the present invention to provide a nasal cannula which obviates or minimises these drawbacks and, furthermore in the case of the user working in a hostile environment, minimises the possibility of the entrainment of gases forming part of the hostile environment.

According to the present invention a nasal cannula for use in administering a gas under pressure through a nasal passage of a user comprises at least one tubular nasal prong assembly including an inner tubular prong having a distal end to be placed in or adjacent the nasal passage and a proximal end for connection to a supply line for the gas and an outer sleeve extending over at least a portion of the inner tubular prong to define with the inner tubular prong an annular passage, the annular passage being in communication with the supply line, the arrangement being such that when gas flows through the supply line most will pass through the distal end of the inner tubular prong for delivery to the nasal passage but some will pass through the annular passage to form a shielding stream.

In one embodiment, the outer sleeve is in the form of a shroud which extends over a portion of the inner tubular prong formed with an array of through holes (i.e. orifices), the arrangement being such that when gas from the supply line passes through the inner tubular prong most will be delivered to the distal end for delivery to the nasal passage but some will exit the array of holes in to the annular passage to form a shielding stream.

Preferably, the flow of gas through the array of holes is no more than 50% of the flow of gas leaving the distal end of the tubular nasal prong.

In a second embodiment the outer sleeve is in the form of a shroud which extends over a portion of the inner tubular prong and is spaced from the inner tubular prong by at least one support.

BRIEF DESCRIPTION OF THE DRAWINGS

An embodiment of the nasal cannula according to the invention will now be described, by way of example, reference being made to the Figures of the accompanying diagrammatic drawings in which.

DETAILED DESCRIPTION OF THE INVENTION

Figure 1:
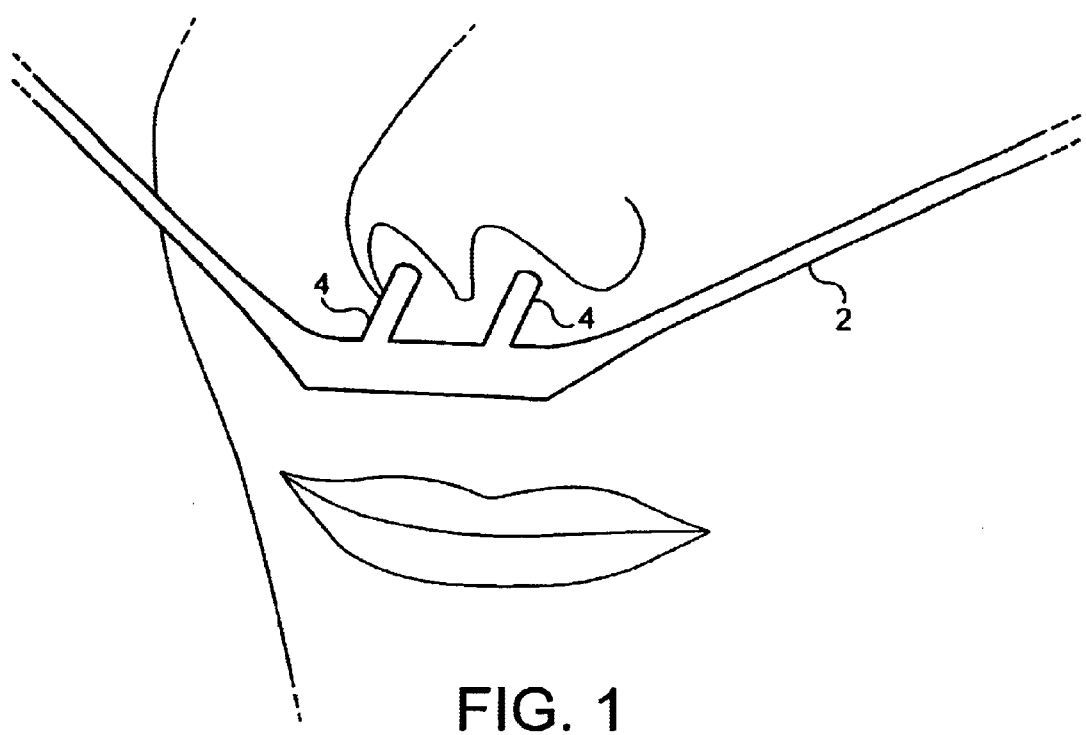
FIG. 1 is a perspective view of a conventional nasal cannula applied to a patient.

Referring first to FIG. 1 where there is shown a conventional nasal cannula which includes a supply line 2 for delivering gas under pressure from a source (not shown) to the proximal ends of two tubular nasal prongs 4. As shown, the distal end of each prong 4 is arranged adjacent a nasal passage of the user and the gas flow emerging from each distal end impinges on the nose and face of the user.

Figure 2:
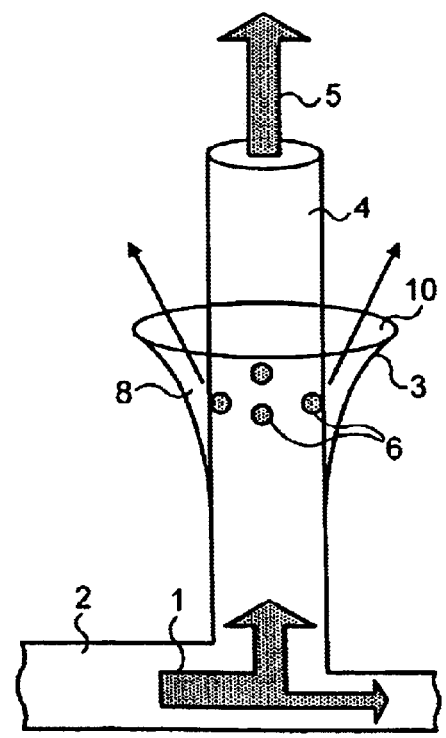
FIG. 2 is a schematic view of one tubular nasal prong assembly forming part of a first embodiment of a nasal cannula according to the present invention.

Referring now to FIG. 2 where like reference numerals denote like parts, according to the present invention the tubular nasal prong 4 forms part of a tubular nasal prong assembly which includes an outer sleeve in the form of a shroud 8 which extends over a portion of the inner tubular nasal prong 4 and defines with the inner tubular nasal prong 4 an annular passage 10. Approximately midway between the proximal and distal ends of the tubular nasal prong 4 there is formed an array of through holes 6, usually no larger than 2 mm diameter. The shroud 8 extends over that portion of the tubular nasal prong 4 in which the array of holes 6 is formed. The shroud 8 is of conical form and generally concentric with the inner tubular nasal prong 4.

In use, with gas under pressure flowing through the supply line 2 a portion of the gas will flow through the inner tubular nasal prong 4 and be split in to two streams, namely a central main jet which extends from the distal end of the prong 4 and a shrouding stream which passes through the holes 6 and extends from the annular passage 10. The central main jet and the shrouding stream are generally concentric so that the shrouding stream shields the main jet from the surrounding gas atmosphere.

The array of holes 6 are sized and numbered so that the central main jet has a relatively high flow rate whilst the shrouding stream has a relatively low flow rate. The shrouding stream minimises the amount of atmosphere entrained allowing for a higher concentration of gas supplied reaching the airways of a user and the avoidance of contamination by polluted atmosphere.

Figure 3:
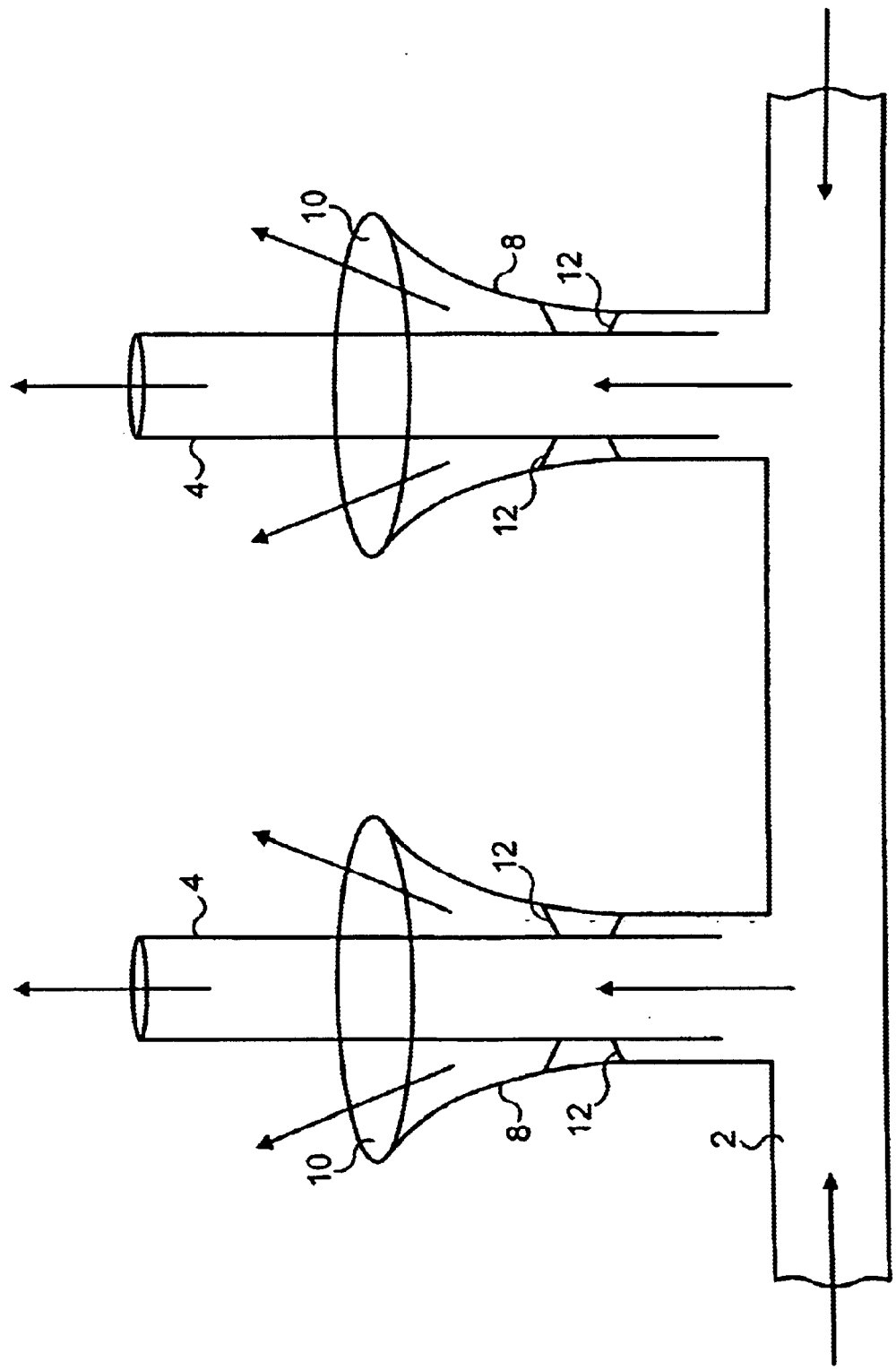
FIG. 3 is a schematic view of two tubular nasal prong assemblies forming part of a second embodiment of a nasal cannula according to the present invention.

Referring now to FIG. 3 where like reference numerals denote like parts, two tubular nasal prong assemblies are shown each of which includes an outer sleeve in the form of a shroud 8 which extends over a portion of an inner tubular nasal prong 4 an annular passage 10. The shroud 8 is generally concentric with the inner tubular nasal prong 4 and is maintained in place, that is, spaced relative to the nasal prong 4 by supports 12.

In use, with gas under pressure flowing through the supply line 2 a portion of the gas will flow through the inner tubular nasal prong 4 whilst the remainder will flow through the annular passage 10. The gas flowing through the tubular nasal prong 4 will form a central main jet for delivery to the nasal passage of a user whilst the gas flowing from the annular passage 10 will form a shrouding stream.

As with the previous embodiment, the tubular nasal prong 4 and the shroud 8 are dimensioned and configured so that the central main jet has a relatively high flow rate whilst the shrouding stream has a relatively low flow rate.

In summary, the configuration of the nasal cannulae subject of the above described embodiments provides two gas streams, one of high flow through the prong and one of lower flow through the shroud which shields the central main jet from the surrounding atmosphere.

Although cannulae have been illustrated and described which provides a tubular nasal prong assembly for each nasal passage of a user, only a single prong assembly may be desired in some applications.

Further, the shrouding stream acts as a reservoir and helps to compensate for varying and random oxygen needs particularly in the case of users not having full mobility.

Since the nasal cannula described with reference to FIGS. 2 and 3 is very efficient it has been found that it can be used with oxygen concentrators which normally could not be used with nasal cannulae, for example, concentrators which produce oxygen concentrations of only 40% by volume. Thus cheaper and smaller oxygen concentrators can be used with the nasal cannula of the present invention.

While this invention has been described with respect to particular embodiments thereof, it is apparent that numerous other forms and modifications of the invention will be obvious to those skilled in the art. The appended claims in this invention generally should be construed to cover all such obvious forms and modifications which are within the true spirit of the present invention.

Having thus described the invention, what we claim is:

1. A nasal cannula for use in administering a gas under pressure through a nasal passage of a user, comprising at least one tubular nasal prong assembly including
    an inner tubular prong having a distal end to be placed in or adjacent the nasal passage and a proximal end for connection to a supply line for the gas and
    an outer sleeve extending over at least a portion of the inner tubular prong to define with the inner tubular prong an annular passage, wherein said outer sleeve is in the form of a shroud which extends over a portion of said inner tubular prong and is spaced from the inner tubular prong by at least one support, the annular passage being in communication with the supply line, the arrangement being such that when gas flows through the supply line most will pass through the distal end of the inner tubular prong for delivery to the nasal passage but some will pass through the annular passage to form a shielding stream.

2. The nasal cannula as claimed in claim 1, in which two tubular nasal prong assemblies are provided one for each nasal passage of a user.

\* \* \* \* \*